United States Patent [19]

Baum

[11] Patent Number: 4,637,386
[45] Date of Patent: Jan. 20, 1987

[54] VENTILATION SYSTEM HAVING TRUE VALVE CONTROL FOR CONTROLLING VENTILATION PRESSURES

[75] Inventor: Marcel Baum, Vienna, Austria

[73] Assignee: Drägerwerk AG, Fed. Rep. of Germany

[21] Appl. No.: 742,608

[22] Filed: Jun. 7, 1985

[30] Foreign Application Priority Data

Jun. 14, 1984 [DE] Fed. Rep. of Germany ....... 3422066

[51] Int. Cl.$^4$ ............................................. A61M 16/00
[52] U.S. Cl. ........................... 128/204.21; 128/204.25; 128/205.24; 137/883
[58] Field of Search ...................... 128/204.21, 204.25, 128/205.24, 205.18, 201.28; 137/883, 885

[56] References Cited

U.S. PATENT DOCUMENTS

| | | | |
|---|---|---|---|
| 2,737,178 | 3/1956 | Fox | 128/204.25 |
| 3,465,752 | 9/1969 | Brychta et al. | 128/204.25 |
| 3,741,208 | 6/1973 | Jonsson et al. | 128/204.21 |
| 3,916,888 | 11/1975 | Buck et al. | 128/204.21 |

FOREIGN PATENT DOCUMENTS 1548585 10/1968 France ........................... 128/204.21

Primary Examiner—Henry J. Recla
Attorney, Agent, or Firm—McGlew and Tuttle

[57] ABSTRACT

A ventilation system with positive and negative ventilation pressures controllable through a control unit is to be improved with respect to its adaptability, in particular in the generation of high pulse repetition frequencies above the natural breathing frequency. A gas transport element is provided in connection with a ring line which contains an inhalation valve in an inspiration branch and an exhalation valve in an expiration branch. The desired improvement is obtained by the fact that the gas transport element is arranged in the ring line with constant direction of delivery. By alternate control of the inhalation valve and exhalation valve in a closed system inspiration and expiration pulses are produced. In addition, a controllable valve unit is indicated in which the inhalation valve and the exhalation valve are actuated as diaphragm valves by combined injector and ejector units of low inertia.

7 Claims, 2 Drawing Figures

VENTILATION SYSTEM HAVING TRUE VALVE CONTROL FOR CONTROLLING VENTILATION PRESSURES

FIELD AND BACKGROUND OF THE INVENTION

This invention relates in general to respirators and in particular to a new and useful ventilation system for persons in which there is a ring line having a gas transport device which is a blower which operates continuously to provide a continuous circulation of the gas from a gas supply and to an improved control providing a control flow in inspiration and expiration branches connected to the ring line.

The invention relates to a ventilation system with positive and negative ventilation pressures controllable through a control unit, which pressures are produced by a gas transport element, a ring line being provided which comprises in an inspiration branch an inhalation valve and in an expiration branch an exhalation valve. In addition, an advantageous controllable valve unit for use in such a ventilation system is provided.

From German Pat. No. 917,210 an apparatus for artificial ventilation is known where a ventilation connection is connected via positively coupled valves controlled as a function of pressure in an open system alternately with the intake side and with the discharge side of an injector.

German Pat. No. 946,258 describes a respirator with an inspiration and an expiration branch, which branches are connected to a pressure blower and with a suction blower. By a gate valve control acting in both branches, positive and negative ventilation pressures of appropriate duration are produced. This, too is an open system, which has the disadvantage of high respiratory gas consumption.

Such systems are not usable because of the control sluggishness of their mechanical parts when a relatively high pulse repetition frequency of the ventilation pulses at high slope steepness is to be achieved.

In German AS No. 24 24 025 a ventilation apparatus with inspiration branch and expiration branch is described, which branches form part of a closed cycle conduit. In the inspiration branch there is an inhalation valve, and in the expiration branch, an exhalation valve. For pressure generation there is used a blower of reversible direction of rotation which is connected alternately to the inspiration branch by its pressure side, and after reversal of direction, to the expiration branch by its suction side. Such an arrangement requires a complicated system of reversing the direction of rotation of the blower and is usable only for relatively slow pulse repetition frequencies.

SUMMARY OF THE INVENTION

The invention proceeds from the technical problem of providing, with the use of a single delivering element, a pneumatically quick-acting ventilation system which permits ventilation at relatively high pulse repetition frequencies (above 200 inspiration pulses per minute-)and with a high slope steepness of the respiration pulses.

For the solution of this problem, it is provided that the gas transport element in the ring line is arranged drivable with constant delivery direction, and that by alternate control of the inhalation valve and exhalation valve inspiration and expiration pulses are generated in a closed system.

Such a ventilation system is adaptable with respect to the pneumatic energy; and, due to the connection of a gas transport element with only one delivering direction, its overall construction is simple. With it, even high-frequency ventilation pulses can be produced with sufficient positive and negative pressure values.

Gas transport elements in ring lines are known in anesthesia equipment through U.S. Pat. No. 4,127,121 among others. There, however, the gas transport element serves exclusively to circulate a flushing gas flow; it does not produce the inspiration and expiration pulses required in a ventilation system.

In the inspiration phase, the gas transport element, which may expediently be designed as a medium pressure blower, produces, in the delivery direction, a positive pressure which, with the inhalation valve open and the exhalation valve closed, forces the respiratory gas into the lung of the ventilated patient via the inspiration branch. Conversely, with the inhalation valve closed and the exhalation valve open, the lung is evacuated via the expiration branch by the negative pressure present at the suction side of the gas transport element. The duration of the inspiration and expiration phases or respectively the magnitude of the produced negative and positive pressures can advantageously be adjusted by a suitable adjustment of the delivery output and of the pulse width for the inspiration and expiration pulses.

In the basic arrangement, the patient to be ventilated is connected via a T-piece to a closed respiratory cycle of the ring line. This respiratory cycle is fed from an external fresh gas source compensates spent oxygen and any leakages in the ring system. The mode of operation here concerned is the volume limited closed one. In further development of the invention it may be provided to install gas storage elements in the inspiration branch and in the expiration branch. In that case a pressure accumulator before the inhalation valve and a vacuum accumulator behind the exhalation valve are maintained under positive pressure and under corresponding negative pressure, respectively. This makes possible spontaneous through breathing, in which during the inspiration phase additional respiratory gas is taken from the pressure accumulator and during the expiration phase is passed into the vacuum accumulator. In this case, spontaneous breathing is superimposed on forced ventilation by the ventilation system.

If by an appropriate adjustment of the control device the inhalation valve as well as the exhalation valve are open, the patient can breathe through spontaneously without forced ventilation. The T-piece forming the ventilation connection may expediently be designed as an injector, if, with the inhalation and exhalation valves open, an intermittent positive pressure ventilation is to be achieved. If the storage capacity of the pressure accumulator and of the vacuum accumulator is within the range of the lung compliance, through breathing is possible without any substantial respiratory resistances. In this mode the ventilation system operates as a half closed system.

In the connecting line between the inhalation valve and the exhalation valve there may expediently be arranged, as an additional safety, at least one compensation valve which opens toward the atmosphere and permits free through breathing when the permissible inspiration pressure is exceeded and when the permissible expiration pressure is not achieved. Instead of one double action compensating valve, two single action compensating valves may be arranged, one compensating valve opening when the permissible inspiration pressure is exceeded and the other compensating valve opening when the permissible expiration pressure is not produced.

While in the mode of operation of the closed system the middle position can be influenced only by dosage of the fresh gas supply, in the mode of the "half-closed system" the middle position can expediently be adjusted for example by arranging in the inspiration branch behind the gas transport element an adjustable overpressure valve and in the expiration branch before the gas transport element an underpressure regulator. The middle position then results from the adjusted overpressure and underpressure and from the ratio of the open times of the inhalation valve and exhalation valve, respectively.

To prevent contamination of the ring line by room air, the underpressure regulator can expediently be provided in the form of a by-pass control between the suction side and pressure side of the blower. In this mode of operation the ventilation system represents a pressure limited half-closed ventilation form.

A controllable valve unit which can be used in the indicated ventilation system, or if desired independently thereof, is expediently constructed so that the inhalation valve and the exhalation valve are designed as diaphragm valves with pneumatic drive, the diaphragm separating an auxiliary control space from a gas conduction space, and where the auxiliary space contains means for overpressure and underpressure generation. In an expedient form of realization, combined injector and ejector pairs are used in such a controllable valve unit. Their nozzles can be connected by the control device to a compressed air source, the control must preferably actuating solenoid valves arranged accordingly. In such a construction, inspiration and expiration pulses of high slope steepness and high pulse repetition frequency can be generated.

The controllable valve unit with its inhalation and exhalation valves can be used in the inspiration branch and expiration branch of any known ventilation apparatus, but it is especially suitable for use in the indicated ventilation system of the initially described kind when high pulse repetition frequencies above the natural ventilation frequency and high slope steepness of the pulses are to be produced.

By the features of the invention, a ventilating system is provided which in the mode of operation as a closed ring system has the special feature of low gas consumption and which moreover can be used selectively as pressure limited closed or volume limited half closed system.

Accordingly it is an object of the invention to provide an improved ventilating system of a respirator and to provide an improved control device therefor.

A further object of the invention is to provide a control device in a ventilating system which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawing, an embodiment of the invention is illustrated schematically.

DESCRIPTION OF THE PREFERRED EMBODIMENTS

Figure 1:
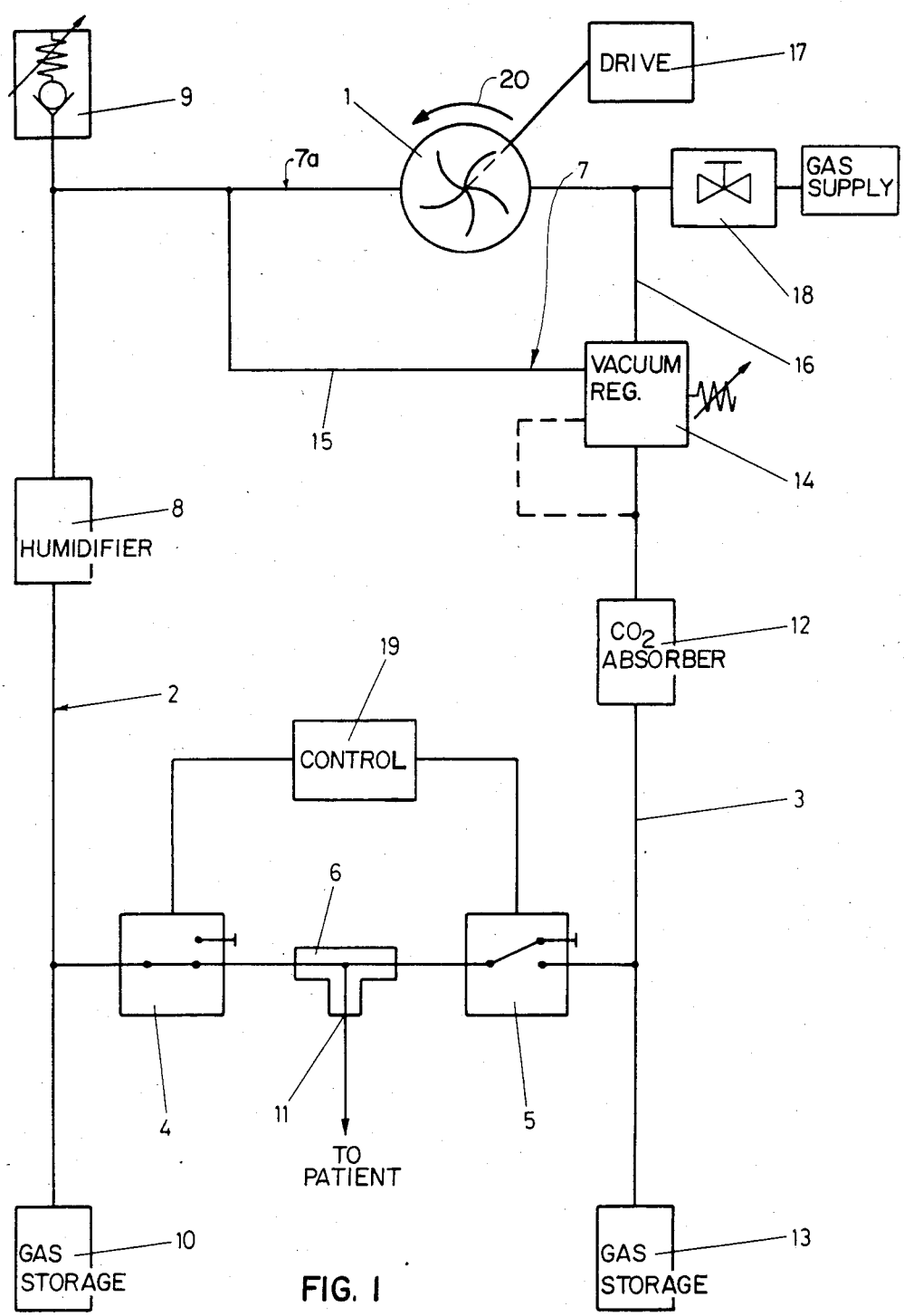
FIG. 1 shows a circuit diagram of a ventilation system in accordance with the invention.
Figure 2:
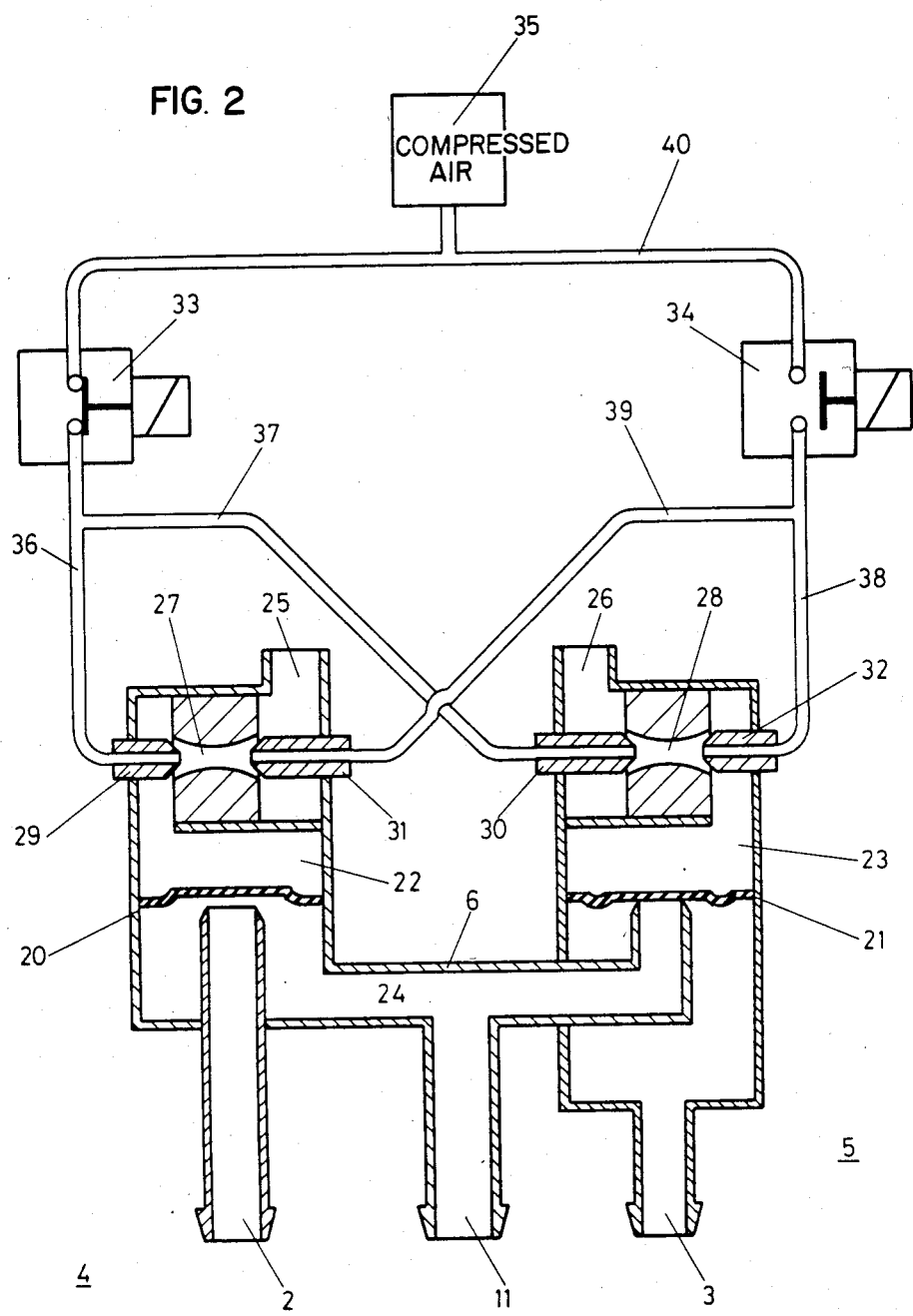
FIG. 2 is a detailed schematic view of the controllable valve unit with the associated switching element for the ventilation system.

Referring to the drawings in particular, the invention embodied therein comprises a ventilating system for persons in which there is a ring line generally designated 7 in FIG. 1 in which gas is moved by a gas transport device such as a blower 1 which is connected at the inlet side of the gas transport to a gas supply through a valve 18. In accordance with the invention an inspiration branch 2 is connected to the ring line 7 adjacent the discharge line 7a of the gas transport device 1 and an expiration branch 3 is connected to the ring line 7 adjacent the inlet line to the gas transport device 1. The pressures in the respective inspiration and expiration lines and through a line 11 which is connectable to the patient, is regulated by an inhalation valve 4 and an exhalation valve 5 connected to respective inspiration and expiration lines 2 and 3 and to respective inhalation valve 4 and exhalation valve 5. A feature of the construction is the T-piece 6 which operates with valves 4,5, from a control 19 which includes a compressed air source 35 as shown in FIG. 2 which acts in respective control spaces 22 or 23 for varying gases which are delivered to inspiration line 2, expiration line 3 and the patient connecting line 11.

In FIG. 1, the gas transport element such as the medium pressure blower 1 is arranged, which together with the inspiration branch 2, the expiration branch 3 as well as the inhalation valve 4, exhalation valve 5 and T-piece 6 is connected to the ring line 7. The direction of rotation of blower 1 and hence the gas transport direction is indicated by an arrow 20. The inspiration branch 2 begins at the outlet of blower 1 and ends at T-piece 6. The expiration branch 3 leads from the T-piece 6 to the suction side of blower 1.

In the inspiration branch 2, in the flow direction behind the blower 1 and before a humidifier 8, there is an adjustable overpressure valve 9. Behind the humidifier 8 and before the inhalation valve 4 a pressure accumulator 10 is connected to the inspiration branch 2. The T-piece 6 connects the inspiration and expiration branches 2 and 3, and by its projection 11 permits ventilation of a person, which can be effected in known manner via a line and to a breathing mask or a tracheal tube (not shown).

The exhalation valve 5 is located at the beginning of the expiration branch 3 and is followed by a $CO_2$ absorber 12. A vacuum accumulator 13 is connected to the expiration branch 3 between the $CO_2$ absorber 12 and the exhalation valve 5. Behind the $CO_2$ absorber 12 lies a vacuum regulator 14. A by-pass line 15 and a line 16 behind the blower 1, bridges the regulator 14 with the suction and pressure side of the blower 1. Before the suction side of blower 1, moreover, a fresh gas transport element in the form of valve 18 is connected from the gas supply to the expiration branch 3 for dosed feeding of respiratory gas into the ring line 7.

The control unit 19, constructed in known manner with electronic components for control of the inhalation valve 4 and of the exhalation valve 5 is used.

By a controllable rotary drive 17 of blower 1, not explained in detail in the drawing, the ventilation system illustrated in FIG. 1 permits an appropriate adaptation to the pressure values and duration of the inspiration and expiration pulses. The vacuum created by blower 1 in the expiration branch 3 is adjustable by the vacuum regulator 14. The repetition frequency and duration of the inspiration phase and expiration phase are determined by the alternate actuation of inhalation valve 4 and exhalation valve 5 by the control unit 19. The overpressure valve 9 permits adjustment of the middle position.

In FIG. 2, the inhalation valve 4 is shown open and the exhalation valve 5 closed. Both valves, 4,5 are diaphragm valves, the diaphragms 20 and 21 separating an auxiliary or control space 22 and 23 from a gas conduction space 24 formed by the remaining inspiration branch 2 and the remaining expiration branch 3.

Arranged in the auxiliary spaces 22 and 23, which lead into the surrounding atmosphere via outlet nipples 25 and 26, are combined injector and ejector units 27 and 28, each comprising an ejector nozzle 29, 32 and an injector nozzle 30, 31. These nozzles are connected via connecting lines 36, 37, 38, 39 to respective solenoid valves 33 and 34. A compressed air source 35, which creates a positive pressure of about 2 to 5 bars, is to be connected to the solenoid valves 33, 34 by a branch connecting line 40.

In the shown inhalation phase with inhalation valve 4 open and exhalation valve 5 closed, a negative pressure is created in the auxiliary space 22 and a positive pressure in the auxiliary space 23. For this purpose the compressed air source 35 is connected by the closed solenoid valve 33 with the ejector nozzle 29 and with the injector nozzle 30 of the combined injectorejector units 27,28. Air is pumped through the ejector nozzle 29 out of the auxiliary space 22 and conducted through the outlet nipple 25 into the surrounding space. With that a vacuum is created which opens the diaphragm 20 and thereby connects the inspiration branch 2 with the projection 11.

The compressed air supply to the injector nozzle 30 brings about the intake of ambient air from the outlet nipple 26 into the auxiliary space 23, so that a corresponding positive pressure is built up, which closes diaphragm 21 and hence shuts off the expiration branch 3. In this state of operation the ejector nozzle 32 and injector nozzle 31 are maintained pressureless by the opened solenoid valve 34.

At the end of the inhalation pulse duration preset in the control unit 19, solenoid valve 34 is closed and solenoid valve 33 is opened. Thus, under reversal of the described processes, there occurs the initiation of the expiration phase by opening of the exhalation valve 5, and at the same time the inhalation valve 4 changes over to the closed position.

Such a controllable valve unit, as described in the foregoing with reference to FIG. 2, is especially low in inertia and therefore can realize the high pulse repetition frequencies desired in high frequency ventilation with high slope steepness of the individual pulses.

While specific embodiments of the invention have been shown and described in detail to illustrate the application of the principles of the invention, it will be understood that the invention may be embodied otherwise without departing from such principles.

What is claimed is:

1. A ventilation system for a person, comprising a ring line having an inlet portion, an outlet portion and a bypass portion connected between said inlet and outlet portions, blower means connected between said inlet and outlet portions for blowing gas from said inlet portion to said outlet portion, drive means connected to said blower means for driving said blower means in only one direction for supplying gas from said inlet portion to said outlet portion, an inspiration line connected to said outlet portion of said ring line for receiving gas therefrom, an inhalation valve connected to said inspiration line, an expiration line connected to said inlet portion of said ring line for supplying gas thereto, an exhalation valve connected to said expiration line, a patient connected between said inhalation and exhalation valves and adapted for connection to a person, and control means connected to said inhalation and exhalation valves for alternately opening said inhalation and exhalation valves to establish inhalation and exhalation for a patient connected to said patient connection and wherein said control means comprises a first housing having an input space connected to said inspiration line, a first valve seat in said input space connected between said inspiration line and said input space, said first housing defining a first control space, a first diaphragm inside first housing separating said first control space from said input space and engageable against said first valve seat for closing communication between said inspiration line and said input space, a second housing having an output space connected to said expiration line, a second valve seat in said output space connected between said output space and said expiration line, said second housing defining a second control space, a second diaphragm in said second housing separating said second control space from said output space and engagable against said second valve seat for closing communication between said output space and said expiration line, a compressed gas source, first and second branch lines connected to said gas source, first ejector nozzle means connected to said first housing for directing a jet stream in a direction to reduce pressure in said first control space to move said first diaphragm in a direction opposite to said first valve seat, second ejector nozzle means connected to said second housing for directing a jet stream in a direction for reducing pressure in said second control space to move said second diaphragm in a direction opposite to said second valve seat, and first injector nozzle means connected to said second housing for directing a jet stream in a direction for increasing pressure in said second control space to move said second diaphragm in a direction toward said second valve seat, and second injector nozzle means connected to said first housing for directing a jet stream in a direction for increasing pressure in said first control space to move said first diaphragm in a direction toward said first valve seat, said first ejector nozzle means and said first injector nozzle means being connected to said first branch line for the simultaneous application of compressed gas thereto, said second injector nozzle means and said second ejector nozzle means being connected to said second branch line for the simultaneous application of compressed gas thereto, the control means including valve means for applying compressed gas alternately to said first and second branch lines, said diaphragms and valve seats forming said inhalation and exhalation valves, and said patient connection being connected between said input space and said second valve seat.

2. A ventilation system according to claim 1 wherein said valve means includes a first solenoid valve in said first branch line and a second solenoid valve in said second branch line.

3. A ventilation system according to claim 1 wherein each housing has a discharge to atmosphere, a Venturi in each housing between said discharge to atmosphere and said control space, said injector nozzles facing an open end of each Venturi communicating with said discharge and said ejector nozzle facing an open end of each Venturi facing said control space, a jet stream from each of said ejector nozzles causing said diaphragm for each housing to move in a direction away from its valve seat and a jet stream from each of said injector nozzles causing each diaphragm to move toward its valve seat.

4. A ventilation system according to claim 1 wherein said blower means comprises a blower having an input connected to said inlet portion and an output connected to said outlet portion.

5. A ventilation system according to claim 1 including a first gas storage connected to said inspiration line and a second gas storage connected to said expiration line.

6. A ventilation system according to claim 5 including a gas supply connected to said inlet portion of said ring line, and an overpressure valve connected to said outlet portion of said ring line.

7. A ventilation system according to claim 5 including a vacuum regulator connected between said bypass portion and said inlet portion and connected to said expiration line for regulating a vacuum in said expiration line.

* * * * *